(12) United States Patent
Fujii et al.

(10) Patent No.: US 9,125,926 B2
(45) Date of Patent: Sep. 8, 2015

(54) VICENIN 2 AND ANALOGUES THEREOF FOR USE AS AN ANTISPASMODIC AND/OR PROKINETIC AGENT

(71) Applicants: Hajime Fujii, Ebetsu (JP); Sybille Buchwald-Werner, Dusseldorf (DE)

(72) Inventors: Hajime Fujii, Ebetsu (JP); Sybille Buchwald-Werner, Dusseldorf (DE)

(73) Assignee: AMINO UP CHEMICAL CO. LTD, Sapporo (JP)

( * ) Notice: Subject to any disclaimer, the term of this patent is extended or adjusted under 35 U.S.C. 154(b) by 0 days.

(21) Appl. No.: 13/997,979

(22) PCT Filed: Nov. 29, 2012

(86) PCT No.: PCT/EP2012/074009
§ 371 (c)(1),
(2) Date: Jul. 26, 2013

(87) PCT Pub. No.: WO2013/079623
PCT Pub. Date: Jun. 6, 2013

(65) Prior Publication Data
US 2013/0303468 A1    Nov. 14, 2013

Related U.S. Application Data

(60) Provisional application No. 61/564,374, filed on Nov. 29, 2011, provisional application No. 61/622,260, filed on Apr. 10, 2012.

(30) Foreign Application Priority Data

Nov. 29, 2011 (EP) .................... 11009430
Apr. 10, 2012 (EP) .................... 12163578

(51) Int. Cl.
| | | |
|---|---|---|
| *A61K 31/70* | (2006.01) | |
| *A61K 31/7048* | (2006.01) | |
| *A61K 36/00* | (2006.01) | |
| *A61K 45/06* | (2006.01) | |
| *A61K 36/535* | (2006.01) | |

(52) U.S. Cl.
CPC ............ *A61K 31/7048* (2013.01); *A61K 36/00* (2013.01); *A61K 36/535* (2013.01); *A61K 45/06* (2013.01)

(58) Field of Classification Search
CPC ........................... A61K 31/7048; A61K 45/06
See application file for complete search history.

(56) References Cited

U.S. PATENT DOCUMENTS 6,503,529 B1 * 1/2003 Fleischner ............... 424/439

FOREIGN PATENT DOCUMENTS

JP    2006238828    9/2006

OTHER PUBLICATIONS

Marrassini, Carla et al. Vicenin-2, a Potential Anti-inflammatory Constituent of Urtica circularis. Journal of Natural Products, Jun. 24, 2011, vol. 74, No. 6, pp. 1503-1507.
Grael, C.F.F. et al. Chemical constituents of Lychnophora pohlii and trypanocidai activity of crude plant extracts and of isolated compounds, Fitoterapia, Jan. 1, 2005, vol. 76, No. 1, pp. 73-82.
Montanha, Jarbas A. et al. Chemical and anti-ulcer evaluation of Jodina rhombifolia (Hook. & Arn.) Reissek extracts. Brazilian Journal of Pharmacognosy, Jan. 2009, vol. 19, No. 1A, pp. 29-32.
Endale, Abebe et al. Quantitative determination of the group of flavonoids and saponins from the extracts of the seeds of Glinus lotoides and tablet formulation thereof by high-performance liquid chromatography. Journal of Chromatography, Aug. 12, 2005, vol. 1083, Nos. 1-2, pp. 32-41.
Bekaii-Saab, Tanios S. et al. Preclinical Experience With Docetaxel in Gastrointestinal Cancers. Seminars in Oncology, Apr. 2005, vol. 32, No. 2, Suppl. 4, pp. S3-S9.
Gilani, Anwarul Hassan et al. Antispasmodic Effects of Rooibos Tea (Aspalathus linearis) is Mediated Predominantly through K+-Channel Activation. Basic & Clinical Pharmacology & Toxicology, Nov. 2006, vol. 99, No. 5, pp. 365-373.
De Ponti, Fabrizio et al. Functional Gut Disorders: From Motility to Sensitivity Disorders, a Review of Current and Investigational Drugs for Their Management. Pharmacology and Therapeutics, Oct. 1998, vol. 80, No. 1, pp. 49-88.
Forbes, Anna L. Irritable bowel syndrome. Medicine, Apr. 27, 2007, vol. 35, No. 5, pp. 267-271.
Fleer, H. at al. Antispasmodic activity of an extract from Plantago lanceolata L. and some isolated compounds. ScienceDirect, Jun. 27, 2007, vol. 14, No. 6, pp. 409-415.
Cinanga, R.K. et al. The spasmolytic activity of extracts and some isolated compounds from the leaves of Morinda morindoides (Baker) Milne-Redh. (Rubiaceae). Journal of Ethnopharmacology, Feb. 3, 2010, vol. 127, No. 2, pp. 215-220.
Lozoya, Xavier et al. Quercetin Glycosides in Psidium guajava L. Leaves and Determination of a Spasmolytic Principie. Archives of Medical Research, Jan. 1, 1994, vol. 25, No. 1, pp. 11-15.
Ragone, Maria Ines et al. The spasmolytic effect of Aloysie citriodora, Palau (South American cedron) is partially due to its vitexin but not isovitexin on rat duodenums. ScienceDirect, Aug. 15, 2007, vol. 113, No. 2. Pages 258-266.
Nagaprashantha, Lokesh DAlasanur et al. Anti-cancer effects of novel flavonoid vicenin-2 as a single agent and in synergistic combination with docetaxel in prostate cancer. Biochemical Pharmacology, Nov. 1, 2011, vol. 82, No. 9, pp. 1100-1109.

(Continued)

*Primary Examiner* — Elli Peselev
(74) *Attorney, Agent, or Firm* — MH2 Technology Law Group, LLP

(57) ABSTRACT

Provided are compositions comprising an active ingredient having antispasmodic and/or prokinetic activity, preferably vicenin 2 or biologically active analogs thereof.

16 Claims, 6 Drawing Sheets

(56) References Cited

OTHER PUBLICATIONS

European Search Report dated May 21, 2012 from European Patent Application No. 12 16 3578, pp. 1-4.

Sena, L. M. et al. Neuropharmacological Activity of the Pericarp of Passiflora edulis flavicarpa Degener: Putative Involvement of C-Glycosylflavonoids. Experimental Biology and Medicine, vol. 234, No. 8, Aug. 1, 2009, pp. 967-975.

* cited by examiner

VICENIN 2 AND ANALOGUES THEREOF FOR USE AS AN ANTISPASMODIC AND/OR PROKINETIC AGENT

CROSS-REFERENCE TO RELATED APPLICATIONS

This application is a U.S. National Stage application of PCT/EP2012/074009 filed 29 Nov. 2012, which claims priority to European Application 12163578.3 filed 10 Apr. 2012, U.S. Provisional Application 61/622,260 filed 10 Apr. 2012, European Application 11009430.7 filed 29 Nov. 2011, and U.S. Provisional Application 61/564,374 filed 29 Nov. 2011, the entire disclosures of which are hereby incorporated herein by reference in their entireties.

TECHNICAL FIELD

The invention relates to food, a dietary supplement or a drug composition comprising an active ingredient, preferably vicenin 2 or biologically active analogues thereof, and especially its beneficial effects for gut.

BACKGROUND OF THE INVENTION

Maintaining optimal digestive health is particularly important to vitality and well being throughout all stages of life. The efficiency of each person's digestive tract can make all the difference in daily energy and overall health. Nearly everybody experiences gastrointestinal discomfort, which affects quality of life.

Symptoms can be bloating, altered intestinal mobility and transit as well as abdominal pain. Many times these symptoms are combined with poor mood, lack of concentration and energy and may consequently prevent people from sleeping, working, exercising and socializing with friends.

Gastrointestinal discomfort is mainly triggered by ileum contractions, which can be caused by several factors. For example, daily stress, food sensitivity and allergies, infections, genetic preposition, altered gut flora or deregulation of brain-gut cross-talk may lead to development of gastrointestinal disorders, dyspepsia or irritations like irritable bowel syndrome (IBS) or inflammatory bowel disease (IBD).

Promoting digestive comfort includes regulation of transit through the gastrointestinal tract and easing pain associated with digestion as well as to support the reduction of causes leading to gastrointestinal discomfort.

Gastrointestinal disorders are divided into structural and functional disorders. Structural diseases, e.g. hemorrhoids, types of colitis, like Morbus Crohn or *C. ulcerosa* as well as colon cancer, can be identified by pathologists and at times cured by medical technology. The nonstructural, functional gastrointestinal disorders, like functional dyspepsia (FD) or IBS are less amenable to explanation or effective treatment. On the one side physicians are traditionally looking for structural evidence in order to make diagnoses and on the other side patients are reluctant to speak clearly about their bowel and its malfunctions. This leads to the situation that functional gastrointestinal disorders are often not diagnosed and treated in a right way.[Ref. 2,5]

More recent scientific studies link the mind and body as part of a system where their dysregulation can produce discomfort and disease. Early in life, genetics, in addition to environmental factors such as family influences on illness expression, abuse, major losses, or exposure to infections, may affect one's psychosocial development in terms of one's susceptibility to life stress or psychological state and coping skills, as well as susceptibility to gut dysfunction—abnormal motility, altered mucosal immunity, or visceral hypersensitivity. Furthermore, these "brain-gut" variables reciprocally influence their expression. Therefore, functional gastrointestinal disorders are a product of this interaction of psychosocial factors and altered gut physiology via the brain-gut axis-[Ref. 5]

Recent drug development target neuropeptides and receptors present in the enteric and CNS to treat stress-mediated effects of CNS modulation of the gut. Under development are drugs targeting serotonin, enkephalins and opioid agonists, substance P, calcitonin gene-related polypeptide, cholecystokinin, neurokinin receptor, and corticotrophin-releasing hormone antagonists, etc.

New drugs for IBS-d targeting the neurotransmitter serotonin and its receptors have been approved. Due to serious side effects, they have only been approved with significant restriction for women only and severe IBD for patients, who have not responded to conventional therapy.[Ref. 3,5]

It is estimated that, 10 to 20 percent of the worlds' total population is affected with IBS. It is estimated that amongst the total affected with IBS, 60% percent are females and 40% are males. It is also believed that about 70 percent amongst those affected with IBS do not seek for doctors' help. IBS is a common problem but most of the people affected with it are either not aware about the problem or tend to avoid to discuss with the physician.

Thus, it is important to develop functional foods and dietary supplement ingredients besides developing drugs.

The whole length of the bowel is controlled by a nervous system, which carries signals back and forward between the gut and the brain, controlling factors such as how fast food is pushed through the intestines. Understanding this basic neuroenteric mechanisms and the brain-gut axis demonstrated the need for an agent ameliorating gastrointestinal irritations at both neurotropic and musculotropic levels.

Despite considerable efforts by academic researchers and pharmaceutical and food industry, the development of novel ingredients to prevent, reduce or treat functional gastrointestinal disorders or to reduce their symptoms has been slow and did not lead to innovations.

The object for the present invention was to provide novel active ingredients to prevent and improve, i.e. ameliorate, functional gastrointestinal discomfort and diseases, like IBS, suitable as functional food, dietary supplement ingredients and drugs.

SUMMARY OF THE INVENTION

The inventors surprisingly found that a composition comprising the active ingredient vicenin 2 or biologically active analogue, i.e. functionally active derivate, thereof has antispasmodic activity inhibiting both at neutrotropic and musculotropic levels as well as prokinetic activity, acting both as reversible cholinesterase inhibitor and acetylcholine agonist.

Thus, the invention describes a new antispasmodic and/or prokinetic agent, which helps to improve gut health and prevent gastrointestinal irritations or diseases, e.g. gastrointestinal discomfort, functional dyspepsia (FD) or irritable bowel syndrome (IBS).

The invention relates to a composition comprising an active ingredient having antispasmodic and prokinetic activity. This ingredient is, preferably, an ingredient derived from a plant and more preferably, vicenin 2 or a biologically active analogue, i.e. functionally active derivate, thereof. However, the invention relates to vicenin 2 or biologically active analogue thereof, which has been obtained by isolation or chemical synthesis, as well.

In particular, the invention relates to a composition comprising as an active ingredient vicenin 2 or biologically active analogue thereof for use in improving gut health.

Furthermore, the invention relates to, in particular, a composition comprising as an active ingredient vicenin 2 or biologically active analogue thereof for use as an antispasmodic and/or prokinetic agent. Preferably, the composition comprises or is derived of a plant preparation comprising the active ingredient and more preferably, the plant preparation has been enriched for the active ingredient.

Antispasmodic and/or prokinetic activity may have a beneficial effect in preventing or improving, i.e. ameliorating, irritable bowel syndrome (IBS), maintaining, i.e. delaying clinical worsening, preventing and/or improving, i.e. ameliorating, functional dyspepsia (FD), reducing or balancing digestive disorders, reducing bloating, reducing distension, reducing passage of gas, reducing stomach rumbling, reducing feeling of fullness, improving, i.e. ameliorating, diarrhea, improving, i.e. ameliorating, constipation, reducing visceral hypersensitivity and/or abdominal discomfort related to pain and/or cramps. In addition, antispasmodic and/or prokinetic activity may have a beneficial effect in maintaining a healthy gut, maintaining a normal digestion, improving gut regularity, supporting healthy gut mobility, bowel movement and/or healthy stool frequency, stool consistency and/or form and/or improving bowel function that may be associated with digestive disorders, IBS, FD, diarrhea, constipation, bloating, visceral hypersensitivity and/or abdominal pain.

Accordingly, an antispasmodic and/or prokinetic agent can have a beneficial effect in preventing or ameliorating, i.e. improving, irritable bowel syndrome (IBS), maintaining, i.e. delaying worsening, preventing and/or ameliorating, i.e. improving, functional dyspepsia (FD), reducing or balancing digestive disorders, reducing bloating, reducing distension, reducing passage of gas, reducing stomach rumbling, reducing feeling of fullness, ameliorating, i.e. improving diarrhea, ameliorating, i.e. improving constipation reducing visceral hypersensitivity and/or abdominal pain. Furthermore, a prokinetic and/or antispasmodic agent may have a beneficial effect in maintaining a healthy gut, maintaining a normal digestion, improving gut regularity, supporting healthy gut mobility, bowel movement and/or healthy stool frequency, stool consistency and/or form and/or improving bowel function that may be associated with digestive disorders, IBS, FD, diarrhea, and/or constipation, bloating, visceral hypersensitivity and/or abdominal discomfort related to pain and/or cramps.

The plant preparation is, preferably, selected from a plant or a group of plants consisting of a *Anethum, Perilla, Urtica, Passiflora, Camelia, Cayaponia, Colocasia, Cydonia, Desmodium, Hordeum, Origanum, Ocimum, Jatropha, Parkinsonia, Peperomia, Piheranthos, Centaurea, Indigo, Bomba, Lychnophera, Asplenium, Chinotto, Citrus, Viola, Trigonella*, Rosemary, Peppermint, Thyme, Basil, Sage, Oregano, *Lavandula, Nipponanthemum, Abrus, Viola, Santalum, Oryza, Scleropyrum, Tulsi, Centaurea, Indigofera, Bombax, Glinus, Lychnophora* and other species belonging to Lamiaceae, Labiatae and Urticaceae, Rosales or Malpighiales or combinations thereof and may be a leaf preparation, a fruit preparation, a seed preparation, a stem preparation, a flower preparation, a bud preparation, a root preparation or a mixture of different parts of the plant. Most preferably, the preparation is a leaf preparation or a preparation of the areal part of the plant.

In a further preferred embodiment the active ingredient is an isolated vicenin 2 obtained by isolation or chemical synthesis.

Furthermore, the invention relates to a use of the active ingredient for maintaining a healthy gut, preventing or improving irritable bowel syndrome (IBS), having a beneficial physiological effect to maintaining, i.e. delaying clinical worsening, preventing and/or improving functional dyspepsia (FD), maintaining a normal digestion, reducing or balancing digestive disorders, improving gut regularity, supporting healthy gut mobility, bowel movement and/or healthy stool frequency, stool consistency and/or form, reducing bloating, reducing distension, reducing passage of gas, reducing stomach rumbling, reducing feeling of fullness, improving bowel function like improved constipation, improving diarrhea, reducing visceral hypersensitivity, abdominal pain and/or cramps and/or inducing antispasmodic and/or prokinetic effects.

In particular, the invention relates to vicenin 2 or a biologically active analogue thereof for use in maintaining a healthy gut, preventing or improving irritable bowel syndrome (IBS), having a beneficial physiological effect to stabilizing, preventing and/or improving functional dyspepsia (FD), maintaining a normal digestion, reducing or balancing digestive disorders, improving gut regularity, supporting healthy gut mobility, bowel movement and/or healthy stool frequency, stool consistency and/or form, reducing bloating, reducing distension, reducing passage of gas, reducing stomach rumbling, reducing feeling of fullness, improving bowel function like improved constipation, improving diarrhea, reducing visceral hypersensitivity, abdominal pain and/or cramps and/or inducing antispasmodic and/or prokinetic effects.

In an additional embodiment, the invention relates to a method for maintaining a healthy gut, preventing or improving, i.e. ameliorating, irritable bowel syndrome (IBS), having a beneficial physiological effect for maintaining, i.e. delaying clinical worsening, preventing and/or improving, i.e. ameliorating, functional dyspepsia (FD), maintaining a normal digestion, reducing or balancing digestive disorders, improving gut regularity, supporting healthy gut mobility, bowel movement and/or healthy stool frequency, stool consistency and/or form, reducing bloating, reducing distension, reducing passage of gas, reducing stomach rumbling, reducing feeling of fullness, improving bowel function like improved, i.e. ameliorating, constipation, improving, i.e. ameliorating, diarrhea, reducing visceral hypersensitivity, abdominal pain and/or cramps and/or inducing antispasmodic and/or prokinetic effects comprising administering a composition comprising as an active ingredient vicenin 2 or biologically active analogue thereof.

The invention further relates to a use of vicenin 2 or biologically active analogue thereof for maintaining a healthy gut, maintaining a normal digestion, improving gut regularity, supporting healthy gut mobility, bowel movement and/or healthy stool frequency, stool consistency and/or form and/or inducing antispasmodic and/or prokinetic effects. This embodiment relates to a use of vicenin 2 or a biologically active analogue thereof for healthy individuals, who wish to e.g. improve well-being after a meal, which is difficult to digest and/or contains compounds which may trigger an allergenic reaction, or before and after stress situations.

In an additional embodiment, the invention provides vicenin 2 or biologically active analogue thereof for use in maintaining a healthy gut, maintaining a normal digestion, improving gut regularity, supporting healthy gut mobility, bowel movement and/or healthy stool frequency, stool consistency and/or form and/or inducing antispasmodic and/or prokinetic effects in a subject suffering from digestive disorders, irritable bowel syndrome, functional dyspepsia, diarrhea, bloating, rumbling, distension, passage of gas, feeling of fullness visceral hypersensitivity, abdominal pain and cramps and/or constipation.

"Maintaining a healthy gut", "maintaining a normal digestion", "improving gut regularity", "supporting healthy gut mobility, bowel movement and/or healthy stool frequency, stool consistency and/or form", "improving bowel function" according to the invention may be associated with digestive disorders, IBS, FD, diarrhea, constipation, bloating, rumbling, distension, passage of gas, feeling of fullness visceral hypersensitivity, abdominal pain and cramps.

In a further embodiment the invention relates to a kit comprising a composition comprising the active antispasmodic and/or prokinetic ingredient vicenin 2 or biologically active analogue thereof and instructions for administration said composition.

Preferably, the composition according to the invention is comprised in a food product, dietary supplement or medicament and the concentration of the active ingredient is from 0.1 µg to 500 µg, preferably of 2.5 µg to 50 µg, preferably from 5 µg to 15 µg or 12 µg to 30 µg, most preferably about 24 µg. Preferably, the food product, dietary supplement, medicament or composition is free of other plant flavonoids or flavonoids of other plants or other plant extracts.

Preferably, the active ingredient is administered at a dose of 0.17-0.42 µg/kg or 0.07-0.3 µg/kg.

Furthermore, the active ingredient may be comprised in globules, pellets, powder formulation, tablets, capsules, stick formulation, sachet formulation or a fluid. The fluid may be in a bottle with a dropper. Besides oral application in capsules, tablets, also powder and granulate formulation being presented as ready to mix blend in a stick package are used. These stick formulation can be directly solved in water.

In an additional preferred embodiment, the preparation is a plant extract, most preferably a liquid or powder extract obtained by extraction.

The composition according to the invention may, additionally, comprise a further agent capable of improving gut health. This further agent may, preferably, be a prebiotic agent, fiber, a probiotic agent, a lipid, a physiologically active fatty acid, a sterol or a sterol ester, a bulking agent, a medicament, an antispasmodic or an anti-inflammatory agent, a plant phenolic a phenolic metabolite, an essential oil and/or a plant preparation.

Preferably, the fiber is an inuline, kiwi fiber, arabinogalactan or psyllium. In an additional preferred embodiment, the plant phenolic is selected from a group consisting of anthocyanins, procyanidins, flavanones, flavonols, tannins and isoflavones. The essential oils, preferably, include mint oil or kiwi fruit oil.

Preferably, the medicament is a further antispasmodic agent, a tricyclic antidepressant, a cholecystokinin-1 antagonist, a serotonergic agent, a benzodiazepine or analogue, a neurokinin antagonist, a Guanylate cyclase-C agonist, a C1-C2 channel activator, a Cl secretion blocker, a GLP1 analogue, a κ-opioid agonist, an antacid, a sodium phosphate, NA reuptake inhibitor, omeprazol analogue, glycocorticoid or an antibiotic.

Preferably, the plant preparation as a further agent is selected from one or more extracts from a group consisting of an extract of *Aloysia triphylla, Hypericum perforatum, Hyperzia serrata, Galanthus nivalis, Salvia officinalis, Panex ginseng, Lippia citriodora, Melissa officinalis, Passiflora incarnate, Passiflora edulis, Bacopa monnieri, Zingiber officinalis, Leucojum aestrum, Concolulus pluricaulis* and *Centella asiatica, Emblica officinalis, Coptidis Rhizoma, Salvia triloba, Piper nigrum, Trigonella foenum-graecum, Cimicifuga racemosa, Salvia miltiorrhiza, Rhodiola rosea, Habranthus jamesonii, Phycella herbertiana, Rhodophiala mendocina, Zephyranthes filifolia, Stephania pierrei, Kaempfera parviflora, Stephania venosa, Crocus sativus, Salvia* species, *Bacopa monnieri, Centella asiatica, Ptychopetalum olacoides, Withania somnifera, Maytenus ilicifolia, Mentha spicata, Coriandrum sativum, Urtica Circularis, Lychnophora pohlii, Lychnophora trypanocidal, Jodina rhombifolio, Aspalathus linearis, Cyclopia* species, *Adansonia digitata, Sclerocarya birrea, Mangifera indica, Actinidia chinensis, Matricaria recutita, Mentha piperita, Plantago lanceolata, Morinda morindoides, Vitis viniferis, Psidium guajava, Aloysia citriodora, Cordyceps sinensis, Laminaria digitata, Cynara scolymus, Carum carvi, Iberis amara, Angelica archangelica, Silybum marianum, Chelidonium majus, Glycyrrhiza glabra, Vaccinium macrocarpon, Vaccinium myrtillus, Vaccinium corymbosum, Vaccinium ashei, Vaccinium angustifolium, Prunus virginiana, Vaccinium parvifolium, Gaylussacia* species, *Vaccinium vitis-idaea, Amelanchier alnifolia* Nutt. and *Salix* species or combinations thereof. In a more preferred embodiment, the plant preparation is selected from *Aloysia triphylla, Lippia citriodora, Melissa officinalis, Piper nigrum, Mentha spicata, Aspalathus linearis, Cyclopia* species, *Adansonia digitata, Mentha piperita, Aloysia citriodora, Vaccinium myrtillus* or combinations thereof.

The invention further relates to a process of producing a preparation of the active ingredient as defined above comprising the steps of:

a) selection of raw plant material,
  b) preparation of the raw plant material,
  c) applying an extraction process using solvent extraction and/or filtration techniques, preferably followed by concentration and/or spray drying of the liquid extract into a powder,
  d) determining the concentration of the active ingredient and
  e) selecting the preparation comprising the active ingredient at a concentration of at least 0.01%.

Preferably, the process comprises an extraction process using aqueous solvent extraction, more preferably water extraction.

Preferably, the solvent is water. In a further preferred embodiment, the extraction is carried out at a temperature of 90° C. to 125° C. and/or the temperature of the solvent is 55° C. above or 70° C. or above.

In a further preferred embodiment, the preparation comprises the active ingredient at a concentration of at least, 0.02%, more preferably, at a concentration of at least 0.1%, 0.15%, 0.2% or most preferably at a concentration of at least 0.2%, 0.25% or 0.3%.

In some cases, the preparation may comprise the active ingredient at a concentration of at least, 0.001%, more preferably, at a concentration of at least 0.002%, 0.005%, 0.008% or preferably at a concentration of at least 0.010%, 0.015% or 0.02%.

In some cases, the preparation may comprise the active ingredient at a concentration of at least, 0.2%, more preferably, at a concentration of at least 0.5%, 1.5%, 3.0% or most preferably at a concentration of at least 2.0%, 3.0% or 5.0%.

Detailed descriptions of conventional methods, such as those employed herein can be found in the literature, for example in the book "Industrial Scale Natural Products Extraction", published in 2011 by Wiley-VCH.

The analytical method to determine the vicenin 2 concentration may be e.g. a chromatographic method called high performance liquid chromatography. High performance liquid chromatography (HPLC) is one of the most popular techniques of analytical chemistry. A UV detector is used, detecting at 320 nm. For determining the concentration of vicenin 2, a vicenin 2 reference or its analogues may be used as reference material. For example, apigenin may be used as reference substance and the vicenin 2 content is calculated via the difference in molecule weight and the slope and intercept of the calibration curve for apigenin.

In the process, the raw plant material is preferably *Perilla* species, more preferably *Perilla frutescens* Britton var.crispa or var.acuta Kudo. The raw plant material is preferably prepared by drying, cutting and/or milling. Extraction can be preferably done with a raw material which particle size was reduced to lower than 2 mm². The solvent may be, preferably, water, methanol, ethanol, propanol, isopropanol, ethyl acetate, hexane, chloroform or dichloromethane. Most preferably an aqueous solution, preferably water, is used since glycosides, like vicenin 2, which have hygroscopic properties, are extracted by hot water more efficiently than alcohol. Moreover, some volatile, allergenic compounds like Perillaldehyde, Methyleugenol and Myristicin, which may occur in targeted species containing vicenin 2 can be eliminated by hot water.

Ratio of raw material to solvent is preferably between 1:100 to 20:100 and more preferably 2:100 to 10:100.

Extraction can be preferably done by room temperature to up to 150° C. Extraction is more preferably carried out from 90° C. to 125° C. In a further preferred embodiment, heat with additional pressure can be used.

In a preferred embodiment the extraction time is 10 min to 2 hours, more preferably from 20 min to 50 min.

Preferably, the plant for the process is selected from the group consisting of *Anethum, Perilla, Urtica, Passiflora, Camelia, Cayaponia, Colocasia, Cydonia, Desmodium, Hordeum, Origanum, Ocimum, Jatropha, Parkinsonia, Peperomia, Piheranthos, Centaurea, Indigo, Bomba, Lychnophera, Asplenium, Chinotto, Citrus, Viola, Trigonella,* Rosemary, Peppermint, Thyme, Basil, Sage, Oregano, *Lavandula, Nipponanthemum, Abrus, Viola, Santalum, Oryza, Scleropyrum, Tulsi, Centaurea, Indigofera, Bombax, Glinus, Lychnophora* and other species belonging to Lamiaceae, Labiatae and Urticaceae, Rosales or Malpighiales or combinations thereof.

The process of the invention provides an extract with a higher concentration of the active ingredient as the prior art processes due to concentration of the active ingredient. The higher concentration is achieved using state of the art extraction equipment, which allows an optimal interaction between the raw material and the extraction solvents. All critical process steps and parameters, for example temperature, are controlled in process at any times and adaptations are continuously possible to ensure highest yield for the active ingredient. Due to the selection of the extraction solvents combined with optimized physical conditions it is possible to diminish unwanted substances which may occur naturally in the different raw materials.

In addition, the invention further relates to an active ingredient preparation obtainable by the process according to the invention. The preparation is, preferably, used as an antispasmodic and/or prokinetic agent to maintain a healthy gut, prevent or improve, i.e. ameliorate, irritable bowel syndrome (IBS), have a beneficial physiological effect to maintain (i.e. delay clinical worsening or stabilize), prevent and/or improve, i.e. ameliorate, functional dyspepsia (FD), maintain a normal digestion, reduce or balance digestive disorders, improve gut regularity, support healthy gut mobility, bowel movement and/or healthy stool frequency, stool consistency and/or form, reduce bloating, reducing distension, reducing passage of gas, reducing stomach rumbling, reduce feeling of fullness, improve bowel function, improve, i.e. ameliorate, constipation, improve, i.e. ameliorate, diarrhea, reduce visceral hypersensitivity, reduce abdominal pain and/or cramps and/or induce antispasmodic and/or prokinetic effects.

DETAILED DESCRIPTION OF THE INVENTION

Figure 1:
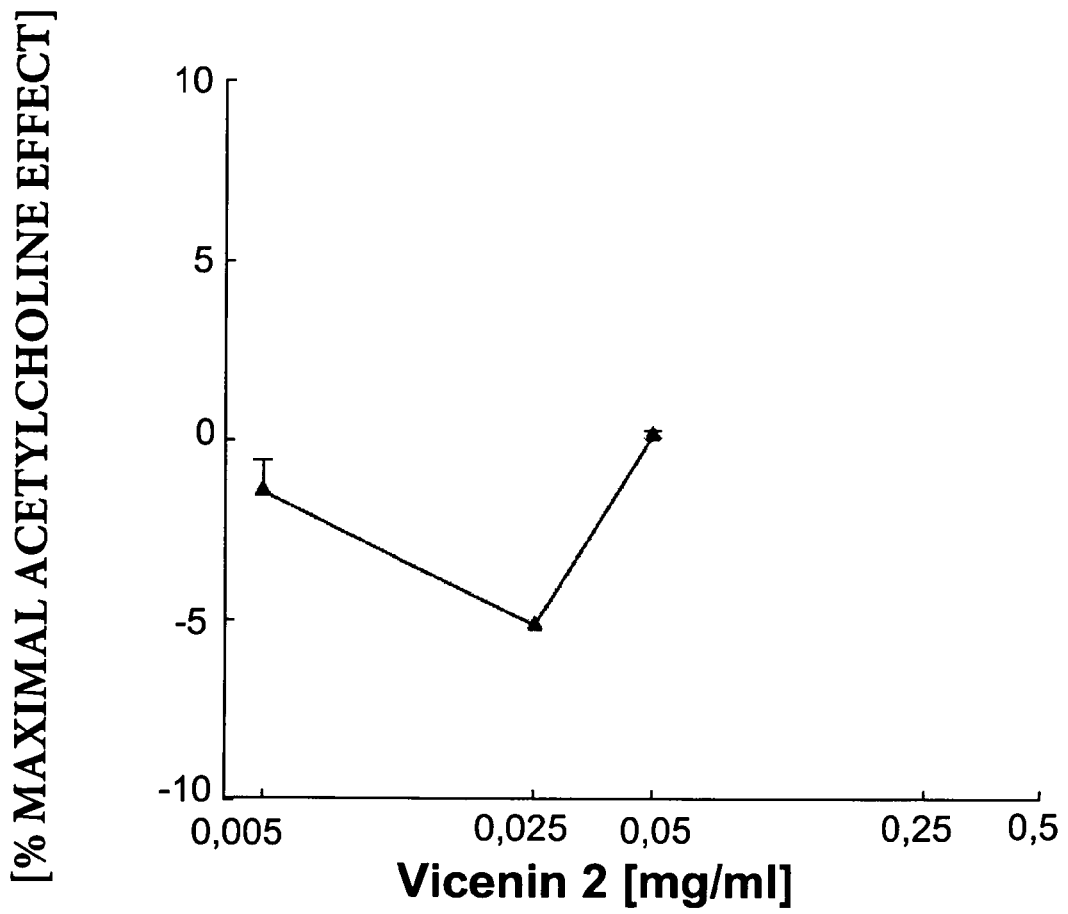
FIG. 1: Effect of vicenin 2 on rat ileum contraction. Data are normalized to the maximum effect of acetylcholine (control 100%). Mean±SE of 1-15 experiments.

The inventors surprisingly found an agent having both antispasmodic effects and prokinetic effects.

In particular, the inventors surprisingly found that vicenin 2 or biologically active analogues thereof have antispasmodic effects to the smooth muscles of the gastrointestinal tract and prokinetic effects supporting GI mobility. This efficacy is very beneficial for gut health, because digestive discomfort and bowel irritation occur, when muscles in the intestine contract faster or slower than normal, causing pain, cramping, bloating, diarrhea or constipation.[Ref.4, 5, 6]

The antispasmodic effect of vicenin 2 or an extract comprising vicenin 2 maintains a healthy gut, prevents or improves irritable bowel syndrome (IBS), has a beneficial physiological effect to maintain, prevent or improve functional dyspepsia (FD), maintains a normal digestion, reduces or balances digestive disorders, improves gut regularity, supports healthy gut mobility, bowel movement, healthy stool frequency, stool consistency and/or form, reduces bloating, improves bowel function, improves constipation, improves diarrhea, reduces visceral hypersensitivity, abdominal pain or induces antispasmodic and/or prokinetic effects.

Typical symptoms for IBS are abdominal hypersensitivity and pain, bloating, wind, discomfort and altered bowel habits (that is, either constipation (IBS-c), diarrhea (IBS-d) or both (alternating IBS), which can destroy the quality of life for those severely affected, but does not lead to life-threatening diseases and does not develop into bowel cancer.[Ref. 4]

Although the exact cause is highly inter-individual, there are certain topics that trigger attacks, including stress, infections, altered intestinal flora, food sensitivity or allergy, irregular mealtimes or lack of dietary fibre. In IBS, the bowel responds with powerful contractions or spasms to stimuli that wouldn't bother other people by simply eating food. The types of IBS and inter-individual causes require a different treatment.

First-line therapy for all forms of IBS includes education, reassurance, exercise, trigger avoidance and dietary modifications.[Ref.1] Psychosocial therapies to reduce daily stress and anxiety are important and include counseling or seminars to learn how to optimize cognitive behavior.

Several functional food or dietary supplement products are available to support a healthy digestion. Current functional food ingredients to maintain a health digestion do address a healthy microbiological flora (probiotics and prebiotics). These ingredients help to reduce flatulence, stuffed feeling, or constipation. In addition a number of herbal therapies have been advertised without evidence supporting their benefit, like for example peppermint oil and TCMs.

Traditional drug therapies generally target single symptoms only. Osmotic laxatives are prescribed for IBS-c and anti-diarrheal agents such as loperamide for IBS-d. The pain associated with IBS can be addressed with antispasmodics such as hyoscyamine or tricyclic antidepressants such as amitriptyline. Overall relief of the multiple symptoms of IBS has rarely been demonstrated with these agents and they are often associated with adverse effects, some of which mimic IBS symptoms.

The invention provides a new important possibility of therapy for gut health not only targeting symptoms but attacking the problems systemically.

DEFINITIONS

It is to be noted that the term "a" or "an" entity refers to one or more of that entity; for example, "an antibody", is understood to represent one or more antibodies. As such, the terms "a" (or "an"), "one or more", and "at least one" can be used interchangeably herein.

By an "isolated" ingredient, variant, or derivative thereof is intended an agent that is not in its natural milieu. No particular level of purification is required. For example, an isolated active ingredient can be removed from its native or natural environment. Synthetically produced active ingredients are considered "isolated" for purpose of the invention, as are native or synthetic active ingredients which have been separated, fractionated, or partially or substantially purified by any suitable technique.

Unless stated otherwise, the terms "disorder" and "disease" are used interchangeably herein.

By "subject" or "individual" or "animal" or "patient" or "mammal", is meant any subject, particularly a mammalian subject, e.g., a human patient, for whom diagnosis, prognosis, prevention, or therapy is desired.

"Maintaining a healthy gut" according to the invention can be understood as maintaining a normal digestion with normal gut mobility and stool frequency, without pain and/or bloating.

"Prevention or improvement, i.e. amelioration, of functional dyspepsia or irritable bowel disease" according to the invention can be understood as that the active ingredient has beneficial physiological effects to prevent or improve, i.e. ameliorate, constipation, diarrhea, or both alternating, abdominal pain and visceral hypersensitivity, bloating and/or discomfort.

"Maintaining functional dyspepsia" means delaying the (clinical) worsening or stabilizing the (state) of the disease.

"Improving, i.e. ameliorating, irritable bowel syndrome" means in this context giving a beneficial effect in a functional gastrointestinal disorder with symptoms of abdominal hypersensitivity and/or pain, bloating, wind, discomfort and/or altered bowel habits (that is, either constipation (IBS-c), diarrhea (IBS-d) or both (alternating IBS), which can destroy the quality of life for those severely affected, but do not lead to life-threatening diseases and doesn't develop into bowel cancer.[Ref. 4] In this context improving, ameliorating or treating can be used interchangeably.

"Constipation" as used herein can be defined as infrequent bowel movements, reduced bowel movement frequency as well as hard to pass bowel movements.

"Inducing antispasmodic effects" can be defined as modulating the cholinergic system so that muscle spasms are suppressed. According to the invention, the stimulation of cholinergic neurons is reduced which results in smooth intestinal muscle relaxation. Preferably, the modulation of a musculotropic local antispasmodic effect is within the gut muscles.

The antispasmodic activity of the active ingredient of the invention was demonstrated to be local in the ileum, muscolotrop, to counteract to triggers like food or food additives. In addition, a neurotropic activity was confirmed which indicated that a spasmolytic effect resulting from stress, communicated via the brain-gut connection, can be positively modulated. This concept is new and before the present invention there was a gap in prevention of gut diseases and conditions and improvement of gut health, which could be closed with the active ingredient of the invention and investigated efficacy.

"Antispasmodic activity" according to this invention can be defined as an activity suppressing muscle spasms, in particular for smooth muscle contractions, especially in tubular organs of the gastrointestinal tract.

"Prokinetic activity" according to this invention can be defined as improvement of gastrointestinal mobility by increasing the frequency of contractions in the intestine, but without disrupting their rhythm.

Vicenin 2 is a flavonoid having a number of derivatizations. Vicenin 2 or its synonyms Apigenin-6,8-di-C-glycoside, 5,7,4'-Trihydroxyflavone-6,8-di-C-glucoside, 5,7-Dihydroxy-2-(4-hydroxyphenyl)-6,8-bis[(2S,3R,4R,5S,6R)-3,4,5-trihydroxy-6 (hydroxymethyl)oxan-2-yl]chromen-4-one with the CAS Registry Number 23666-13-9 is a flavonoid found in a number of plant species. Vicenin 2 can be found i.a. in *Perilla* species, *Urtica* species, *Passiflora* species, *Camelia* species, *Cayaponia* species, *Colocasia* species, *Desmodium* species, *Hordeum* species, *Origanum* species, *Ocimum* species, *Jatropha* species, *Parkinsonia* species, *Peperomia* species, *Piheranthos* species, *Centaurea* species, *Indigo* species, *Bomba* species, *Lychnophera* species, *Asplenium* species, *Chinotto* species, *Citrus* species, *Viola* species, *Trigonella* species, species belonging to the Lamiacea, Labiatae and e.g. Rosemary, Peppermint, Thyme, Basil, Sage, Oregano, Lavandula, Nipponanthemum, Abrus, Viola, Santalum, Oryza, Scleropyrum, Tulsi, Centaurea, Indigofera, Bombax, Glinus, Lychnophora, and species belonging to Urticaceae, Rosales or Malpighiales.

The standard process to purify vicenin 2 out of plant material is based on different chromatographic methods known by person skilled in the art and consequently, vicenin 2 may be identified by spectroscopy. These processes can be reviewed in several publications.[Ref. 15, 16]

So far the literature describes that vicenin 2 has an anticancer, anti-inflammatory and antinociceptive effect.[Ref. 7, 8, 9,]

"A plant extract comprising vicenin 2 or biologically active analogue thereof" is herein understood according to this invention to be an extract comprising vicenin 2 at a concentration which can be measured. The plant extract or preparation preferably comprises the active ingredient preferably at a concentration of at least 0.001%, 0.002%, 0.005%, 0.008%, 0.010%, 0.015% or 0.02% or from 0.02% to 0.3%, more preferably from 0.1% to 0.2% and most preferably from 0.15% to 0.2%.

In some cases, the preparation may comprise the active ingredient at a concentration of at least, 0.001%, more preferably, at a concentration of at least 0.002%, 0.005%, 0.008% or preferably at a concentration of at least 0.010%, 0.015% or 0.02%.

In some cases, the preparation may comprise the active ingredient at a concentration of at least, 0.2%, more preferably, at a concentration of at least 0.5%, 1.5%, 3.0% or most preferably at a concentration of at least 2.0%, 3.0% or 5.0%.

As used herein "functionally active derivatives", "functionally active analogues", "biologically active derivates" or "biologically active analogues", which are used interchangeably herein, of vicenin 2 relate to structurally similar compounds to vicenin 2, e.g. flavone c-glycosides or flavone o-glycosides, in particular, apigenin 7-O-β-glucuronide, apigenin-7-O-[β-glucuronosyl (1→2 β-glucuronide], luteolin 7-O-[β-glucuronosyl(1→2) β-glucuronide], luteolin 7-O-β-glucuronide or scutellarein O-β-glucuronide (scutellarin), which also show antispasmodic and/or prokinetic activity. The antispasmodic and/or prokinetic activity can be measured as shown in the examples. There are several possibilities to investigate antispasmodic and/or prokinetic activity, which are known to the skilled person. In vitro studies, like receptor binding assays or enzyme inhibition studies, are standard methods to identify activity and its mode of actions. In addition, ex vivo studies are used to confirm the efficacy within the targeted area, e.g. as shown in example 1, where the antispasmodic effect was investigated in isolated rat intestines. Furthermore in vivo animal and in vivo human studies are used to confirm the effect within the biological system. Measures to quantify antispasmodic and prokinetic activity within in vivo studies which target gastrointestinal mobility are, for example, stool frequency and stool consistency. These kinds of studies are well known for the person skilled in the art.

"The active ingredient" as used herein relates to an ingredient having antispasmodic and/or prokinetic activity, preferably, vicenin 2 or functionally or biologically active derivative or analogue thereof.

In order to induce the antispasmodic and/or prokinetic effects the concentration of the active ingredient in the composition is 0.1 μg to 500 μg, preferably 2.5 μg to 50 μg, more preferably 5 μg to 15 μg or 12 μg to 30 μg, preferably about 24 μg vicenin 2 or analogue thereof.

The composition is a plant preparation or plant extract, most preferably a liquid or powder extract obtained by extraction and comprising vicenin 2.

The composition according to the present invention can be comprised in a functional food product, dietary supplement or in a drug.

"A functional food product" according to this invention is understood to be a food, beverage or infant formular product, which offers, in addition, to nutritional value a health benefit, which supports and improves health and wellbeing or helps to reduce the risk to develop a disease.

"A dietary supplement product" according to this invention are food products in form of pill, tablet, capsule, pellet, globule, powder or liquid form, stick formulations, powder formulations, sachet formulations, which are meant to be taken by mouth, and contain substances like vitamins, minerals, foods, plan preparations, amino acids and are intended to supplement the usual intake of these substances via the normal diet.

"A medicament/drug/medicine" according to this invention is any substance with the potential to prevent or cure disease or enhance physical or mental welfare. If not stated otherwise the term "drug", "medicine", or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals; and (B) articles, medicines and preparations (other than food) intended to affect the structure or any function of the body of man or other animals; and (C) articles intended for use as a component of any article specified in clause (A) and (B). The term "drug", "medicine" or "medicament" shall include the complete formula of the preparation intended for use in either man or other animals containing one or more "agents", "ingredients", "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug", "medicine", or "medicament" at an intended target location within the body of man or other animals, e.g., at the skin, in the stomach or the intestine. The terms "agent", "compound" or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

As used herein, the terms "treat" or "treatment" refer to both therapeutic treatment and prophylactic or preventative measures, wherein the object is to prevent or slow down (lessen) an undesired physiological change or disorder, such as the development of a gut disease. Beneficial or desired clinical results include, but are not limited to, alleviation of symptoms, diminishment of extent of disease, stabilization (i.e., not worsening) state of disease, delay or slowing of disease progression, amelioration or palliation of the disease state, and remission (whether partial or total), whether detectable or undetectable. Those in need of treatment include those already with the condition or disorder as well as those prone to have the condition or disorder or those in which the manifestation of the condition or disorder is to be prevented.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices.

For example the public database "Medline" or "Pubmed" may be utilized, which is hosted by the National Center for Biotechnology Information and/or the National Library of Medicine at the National Institutes of Health. Further databases and web addresses, such as the virtual library "Martindale's center" are known to the person skilled in the art and can also be obtained using internet search engines.

Several documents are cited throughout the text of this specification. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The above disclosure generally describes the present invention. A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way.

The practice of the present invention will employ, unless otherwise indicated, conventional techniques of plant biology, chemistry, biochemistry, physiology and pharmacology which are within the skill of the art.

Example 1

Vicenin 2 has Antispasmodic Activity

Methods and Compound

An isolated vicenin 2 compound was tested for its antispasmodic effect with respect to the cholinergic system and with respect to nonspecific contraction mediated by $Ba^{++}$. Therefore, rat ileum was precontracted with increasing concentrations of either acetylcholine or $Ba^{++}$. The shift of either concentration response curve by the compound was determined. As positive controls either atropine or papaverine were used depending on the type of experiment. The isolated vicenin 2 showed a good solubility.

Calculation of Concentrations to be Used in the Experiments:

The dose of vicenin 2 for humans was estimated to be between 5 and 15 µg/70 kg b.w. which will correspond to 0.071 and 0.214 µg/kg b.w. Due to the increased metabolism in rodents compared to humans the doses were calculated as approx. between 0.5 and 1.49 µg/kg b.w. The central (blood) compartment (hydrophilic extracts) is approx. 7% of whole body volume, i.e. between 0.5/70 g and 1.4 µg/70 g blood. Since blood is in direct contact with ileum, a concentration of 7 to 20.86 µg/kg (0.007 to 0.021 µg/g) is expected for ileum. Note: calculations were not corrected for specific gravity (density) of liquids (possibly differing from exactly 1.0) and for absorption (assumed to be 100%; no data available). Therefore, it was reasonable to translate these in vivo calculations into the in vitro experiments and in these experiments 10 and 100 µl of a stock solution per 10 ml incubation bath were used. Therefore, the final concentrations of AUC-V were 0.005 or 0.05 mg/ml bath volume.

Acetylcholine sulfate and Barium chloride were from Roth, Karlsruhe, Germany, and Sigma-Aldrich Chemie, Deisenhofen, Germany. All other reagents and compounds used for incubations were obtained from Roth, Karlsruhe, Germany.

Rat Ileum

Under a protocol approved by the Animal Care and Use Committee of Munster, Germany, male and female rats (Charles River, Sulzfeld, Germany) weighing 200 to 320 g were used. The rats were anesthetized ($CO_2$). The proximal ileum was removed, washed and placed in Krebs-Henseleit solution. 1 cm segments were placed in 10 mL organ baths with a resting tension of 1.0 g (preload). One end was attached to a force displacement transducer (lever transducer B40, Typ 373) combined with a two-channel amplifier (type 301, Hugo Sachs Elektronik, March, Germany); for the recording of tension changes a multi-pen recorder was used (Rikadenki Kogyo, Tokio, Japan). The composition of Krebs-Henseleit solution was (mM): NaCl 118.1, KCl 4.7, $CaCl_2$ 2.5, $MgSO_4$ 1.2, $NaHCO_3$ 25 and glucose 5.6. The solution was kept at 37° C., pH 7.4 and gassed with carbogen (a 95% $O_2$/5% $CO_2$ mixture). Equilibration time for the ileum before starting the experiment was at least 30 min. After the tissues had been pre-treated with the extracts for 3 min cumulative concentration response curves using either acetylcholine or barium ion were recorded isotonically in the organ bath, and the effect was allowed to reach a steady state at each concentration.

The results were normalized to 100% (maximum effect of either acetylcholine or barium ion alone).

Statistical Analysis

Differences between entire curves were obtained by comparing F-values of the best fitted curves by using GraphPad-Prism (version 3.00, GraphPad Software, Inc., 1999). $P<0.05$ was regarded as statistically significant.

Results

As shown in FIG. 1, vicenin 2 induced a slight (not significant) relaxation from its own. The data are shown as % of maximum acetylcholine effect (controls in the presence of 10 µg/ml). This means that it lacks a direct spasmolytic effect.

Figure 2:
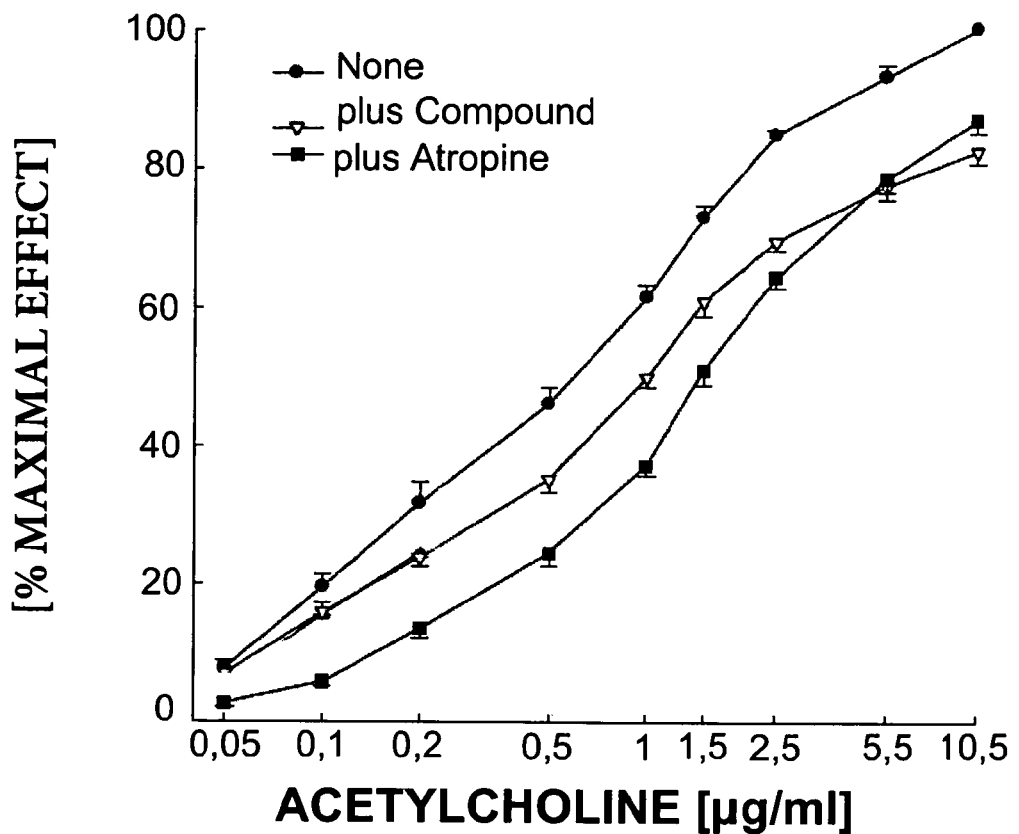
FIG. 2: Effect of AUC-V (0.005 mg/ml) on rat ileum contraction induced by increasing concentrations of acetylcholine. Data are normalized to the maximum effect of acetylcholine (control 100%). Atropine ($5\times10^{-5}$ mg/ml) was used as a positive control. Mean±S.E. of 4 independent experiments. The acetylcholine curves modulated by compound AUC-V and atropine were significantly different from the acetylcholine curve (no further additions).

Next the effect of various acetylcholine concentrations and the interaction with vicenin 2 are shown (FIG. 2). Low concentrations of the compound (0.005 mg/ml) shifted the acetylcholine curve to the right in a competitive manner. The data indicates a neurotropic antispasmodic effect. Atropine (positive control) shows the expected competitive neurotropic antispasmodic effect indicating that the setup of experiment is working. The use of atropine is mimicked by the marketed N-butylscopolamine (Buscopan®).

Figure 3:
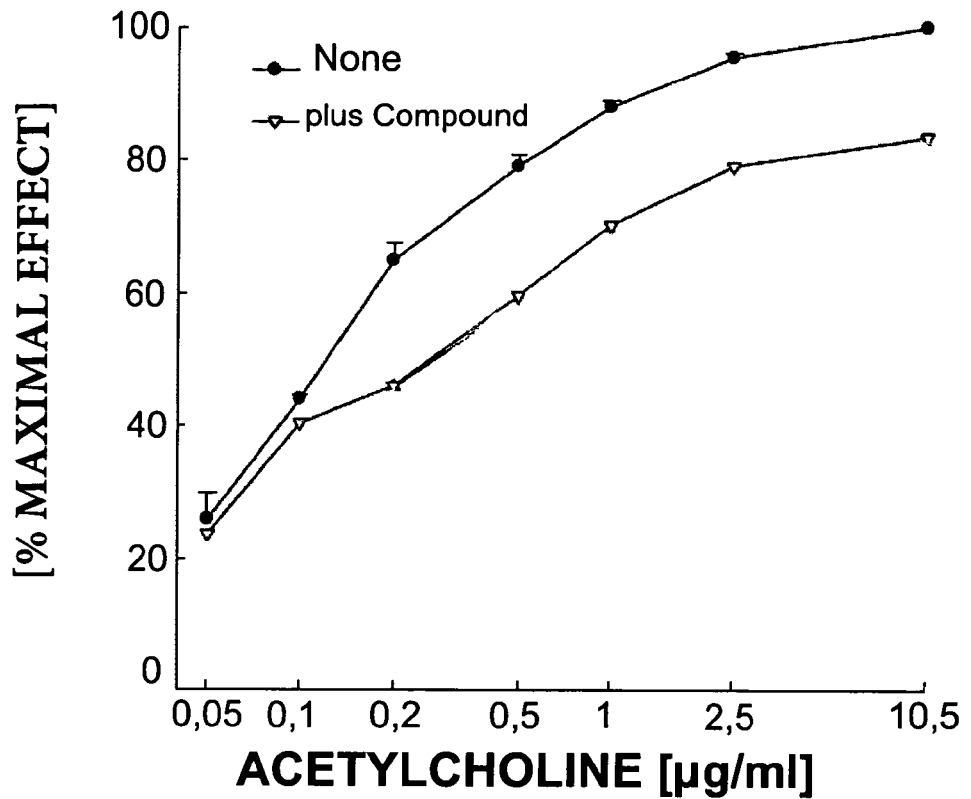
FIG. 3: Effect of compound AUC-V (0.05 mg/ml) on rat ileum contraction induced by increasing concentrations of acetylcholine. Data are normalized to the maximum effect of acetylcholine (control: 100%). Mean±S.E. of 7-10 independent experiments. Curves induced by AUC-V are significantly different from the acetylcholine curve (nor further additions).

These experiments were repeated while the concentration of vicenin 2 was increased 10-fold, from 0.005 to 0.05 mg/ml (final bath concentration). The data are shown in FIG. 3. Increasing the concentrations of the compound results in a stronger rightward and downward shift of the acetylcholine curve, which indicates a concentration dependent effect.

Figure 4:
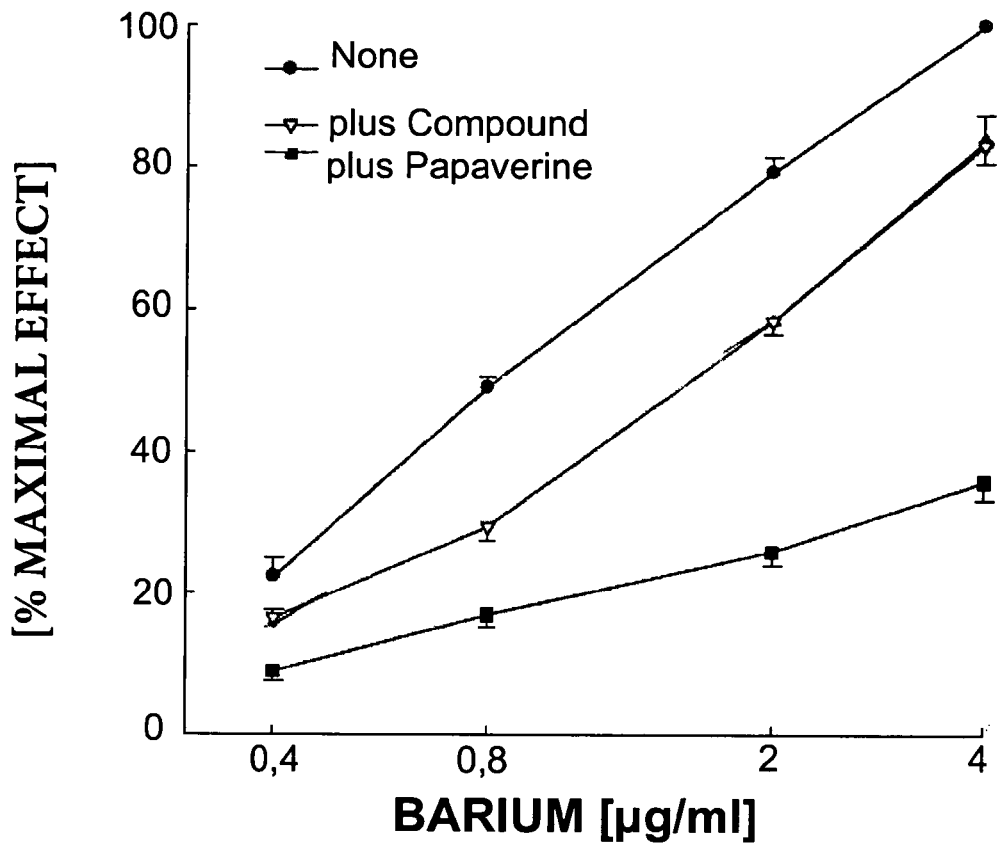
FIG. 4: Effect of compound AUC-V (0.005 mg/ml) on rat ileum contraction induced by increasing concentrations of barium ion. Papaverine ($4\times10^{-2}$ g/ml) was used as positive control. Data are normalized to the maximum effect of barium ion (control: 100%). The curves mediated by compound AUC-V and papaverine were significantly different from the acetylcholine curve without additions. Mean±S.E. of 4 independent experiments
Figure 5:
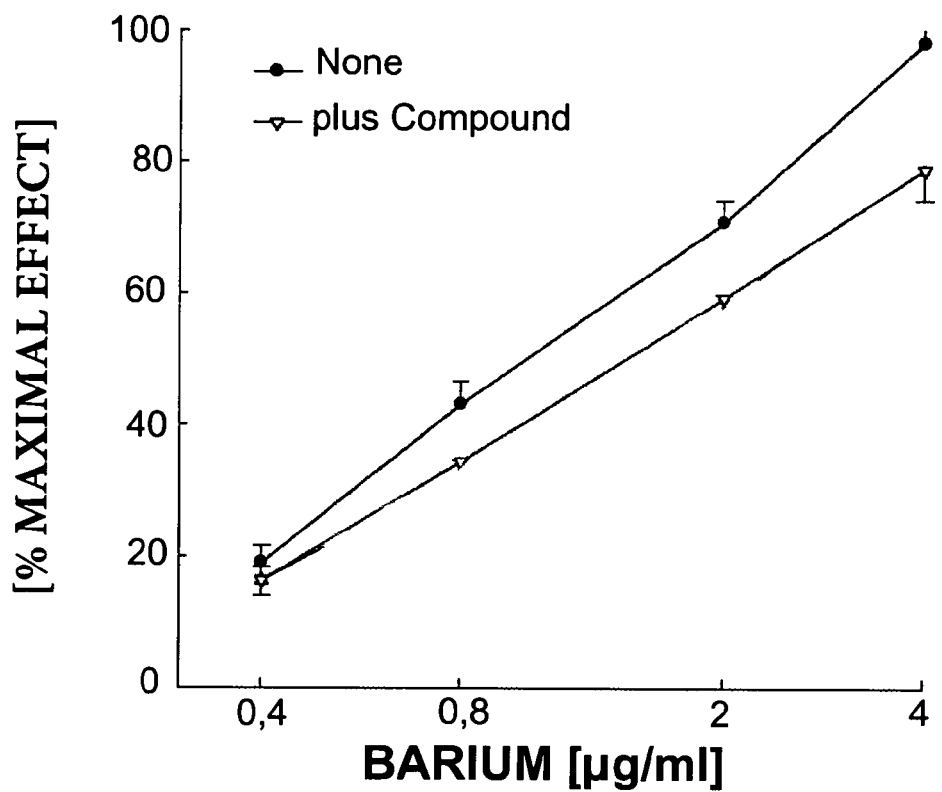
FIG. 5: Effect of AUC-V (0.05 mg/ml) on rat ileum contraction induced by increasing concentrations of barium ion. Data are normalized to the maximum effect of barium ion (control: 100%). Curves induced by AUC-V are significantly different from the acetylcholine curve with no further additions. Mean±S.E. of 6-9 independent experiments.

Next the effect of various $Ba^{++}$ concentrations and the interaction with vicenin 2 is shown (FIG. 4). Low concentrations of the compound (0.005 mg/ml) shifted the $Ba^{++}$ curve downwards indicating a non-competitive antispasmodic effect. The data indicate a musculotropic antispasmodic effect. Papaverine (positive control) shows the expected non-competitive musculotropic antispasmodic effect indicating that the setup of experiment is correct and working These experiments were repeated while the concentration of the compound was increased 10-fold, from 0.005 to 0.05 mg/ml (final bath concentration). The data are shown in FIG. 5. The compound shows additional results in a rightward and downward shift of the $Ba^{++}$ curve which indicates a non-competitive inhibition (antispasmodic effect) of the $Ba^{++}$ effect. The effects were as strong as compared to these at the lower concentrations shown in FIG. 5.

Discussion

Extracts and drugs have to be tested in two ways: first whether they have an effect from their own (so-called spasmolytic effect), and second whether they have an antispasmodic effect against compounds inducing smooth muscle contraction.

The antispasmodic effect on smooth muscles leading to a relief from gastrointestinal symptoms including bowel disease symptoms can be achieved by two types of effective compounds: they should either have neurotropic or musculotropic antispasmodic effects or even both. Physiologically a neurotropic effect is mediated via acetylcholine; a musculotropic effect is mediated via e.g. toxic compounds. Surprisingly, the compound vicenin 2 has an antispasmodic activity, inhibiting neurotropic and musculotropic activity. Importantly, its effects show a concentration dependency with respect to its neurotropic antispasmodic activity. Its effects are not as strong as typical lead compounds (positive controls): in this case the effects were minor compared to either atropine (acetylcholine experiments) or papaverine ($Ba^{++}$ experiments).

Summarizing, the compound vicenin 2 has antispasmodic effects using two different mechanisms of action probably helping when there is an irregular contraction leading to GI symptoms. This effect was surprising since other flavonoid glycosides have been described to have weaker effects.

Example 2

Vicenin 2 has Prokinetic Activity

Methods and Compound

Purpose of this example was the evaluation of the acute neuroactive effects of vicenin 2 (named AUC-V) on the neuronal activity of murine frontal cortex networks in vitro by means of electrophysiological multi-channel recordings.

Therefore, in a first step the dose-effect curve of vicenin 2 was plotted by means of cumulatively increasing the substance concentration, so that the spectrum of activity of the substance is optimally covered with 9 concentrations. Concentration from 100 fg/ml, 10 pg/ml, 100 µg/ml, 1 ng/ml, 100 ng/ml, 1 µg/ml, 10 µg/ml, 100 µg/ml and 300 µg/ml were used.

Subsequently, the measurements of the dose-effect curve of the test substances were repeated at least 10 times. The recorded electrical activity patterns were characterized by 200 features and their changes were statistically evaluated.

Afterwards, a further analysis was carried out through a pattern-recognition analysis and through comparison with NeuroProof database to determine relevant mechanisms involved in the frontal cortex activity pattern induced changes by each substance.

Materials

The chemicals 5-fluoro-2'-deoxyuridine+uridine (FDU), and poly-D-lysine were ordered from Sigma-Aldrich Chemical GmbH (Steinheim, Taufkirchen, Germany). DNase I (from bovine pancreas), and laminin were purchased from Roche (Mannheim, Germany), fetal bovine serum from Pan Biotech GmbH (Aidenbach, Germany), and accutase from PAA (Germany). Horse serum and Dulbecco's Modified Essential Medium (DMEM) were ordered from GIBCO BRL (Paisley, UK).

Microelectrode Array Neurochips

The microelectrode array neurochips (MEA neurochips) were provided by the Center for Network Neuroscience (CNNS) at the University of North Texas. These 5×5 $cm^2$ glass chips have a central recording matrix with 64 passive electrodes and indium tin oxide conductors. The hydrophobic insulation material surface was activated by a brief butane flame pulse through a stainless steel mask. Thus, cell attachment on a confined adhesive region (5 mm diameter centered on the electrode array) is ensured. The activated surface regions were coated with poly-D-lysine (25 µg/ml; 30-70 kD) and laminin (16 µg/ml). Fabrication techniques and culture methods have been described previously.

Cell Culture

Frontal cortex tissue was harvested from embryonic day 15, or day 14 chr:NMRI mice. After ethyl ether anesthesia, mice were sacrificed by cervical dislocation according to the German Animal Protection Act §4. Neuronal tissue was cultured including the use of DNase I (8000 units/ml) and accutase (10 U/ml) for tissue dissociation. The tissue was dissociated enzymatically with accutase and mechanically with transfer pipettes. The cells were resuspended in DMEM 10/10 (10% horse and 10% fetal calf serum) at a density of $1.0 \times 10^6$ cells/ml, and 400 µl were seeded onto MEA surfaces. Cultures were incubated at 37° C. in a 10% $CO_2$ atmosphere until ready for use, which usually is four weeks to three months after seeding. Culture media were replenished three times a week with DMEM containing 10% horse serum. Like in the tissue of origin, networks develop from a mixture of different types of postmitotic neurons and glial cells. The glial cells have important auxiliary functions for the metabolism and for supplying the neurons with ions and nutrients. The developing co-cultures were treated with 5-fluoro-2'-deoxyuridine (25 µM) and uridine (63 µM) for 48 h to prevent further glial proliferation.

The cells growing directly on the neurochips emerge as natural neuronal networks. These are composed of a mixture of neurons and glial cells comparable to the tissue of origin, whereas in interaction with the neurons, the glial cells fulfill various metabolism and transport functions. The neurons were coupled electrically to the neurochip electrodes whereby the action potentials of the cells can be recorded and their amplitudes and the electrical activity pattern can be evaluated.

Activity starts after approximately three to four days in vitro in form of random spiking Only after establishing a stable activity pattern after 4 weeks, the neuronal networks are employed in substance testing. For this study, cultures between 26 and 29 days in vitro were used.

Multichannel Recording

For extracellular recording, MEA neurochips were placed into sterilized constant-bath recording chambers and maintained at 37° C. Recordings were made in DMEM/10% horse serum. The pH was maintained at 7.4 with a continuous stream of filtered, humidified airflow with 10% $CO_2$. Sets of preamplifiers were positioned to either side of the recording chamber. Recording was performed with the multichannel acquisition processor system, a computer-controlled 64-channel amplifier system (Plexon, Inc., Dallas, Tex., USA) providing programmable amplification, filtering, switching, and digital signal processing of microelectrode signals. The total system gain used was 10K with a simultaneous 40 kHz sampling rate. The signals routinely recorded by these neurochips are located in a range of 15-1800 µV.

The multichannel signal acquisition system delivered single neuron spike data. Spike identification and separation were accomplished with a template-matching algorithm in real time. This allowed the extracellular recording of action potentials from a maximum of 256 neurons simultaneously.

The action potentials, or "spikes", were recorded in spike trains and are clustered in so-called bursts. Bursts were quantitatively described via direct spike train analysis using the program NeuroEXplorer (Plexon Inc., Dallas, Tex., USA) and in-house programs. Bursts were defined by the beginning and end of short spike invents. Maximum spike intervals defining the start of a burst were adjusted from 50 to 150 ms and maximum intervals to end a burst from 100 to 300 ms.

Multiparametric Data Analysis

The high content analysis of the network activity patterns provided a multiparametric description characterizing the changes in four categories: general activity, burst structure, synchronicity and oscillatory behavior. The substance-specific activity changes were quantified by calculating for each stable activity phase after substance application a total of 200 activity-describing spike train parameters for these four categories below.

Statistical Analysis

Results are expressed as series means±SEM. The absolute parameters' distributions were tested for normality. The level of significance after compound application was assessed using Student's paired t-test. Significance between two substances or relative to a contained solvent (e.g. DMSO) was assessed using Student's unpaired t-test. $P<0.05$ was considered statistically significant.

For direct comparability all parameters were normalized for each experiment and each experimental treatment with regard to the corresponding values of the reference activity (native or after receptor blockade if applicable set to 100%).

For each experiment, the changing spike rate as a function of the concentration was fitted to a one-sigmoidal or multiphasic-sigmoidal dose-response curve given by the equation:

$$y = y_{START} + \frac{y_{END} - y_{START}}{1 + 10^{[log(EC_{50}) - log(x)]*nH}}$$

determining the values of the effective concentration causing 10, 50, and 90% effect ($EC_{10}$, $EC_{50}$, and $EC_{90}$) and of the slope (Hill coefficient nH; describes the slope of the curve: a high value corresponds to steep decline which might correspond to functional neurotoxicity). In case of multiphasic response due to several mechanisms of action, the right term is repeatly added for further phases.

Pattern Recognition and Classification

To clarify the mode of action of the test substance on the activity of cortical networks these experiments were further analyzed using methods of pattern recognition. For each stable concentration activity phase we normalized the 200 spike train parameters by the native reference activity. These data records were computed for the test substances and the reference substances.

Using a feature selection algorithm, on the basis of the reference substances, the 40 most descriptive parameters for all 200 spike train parameters were selected. The rankings of activity features using various score methods based on classification experiments and compared their total correct predictions were calculated. In this manner, the best results for a MDL (minimal description length) modified algorithm were obtained. A training data set with these 40 spike train parameters was established in the form of data records from the reference substances. An artificial neuronal network, multi layer feed forward network and back propagation algorithm without hidden units was then trained. The respective data records of the four substances were all subsequently classified. A classification against 105 substances in the database was carried out.

Figure 6:
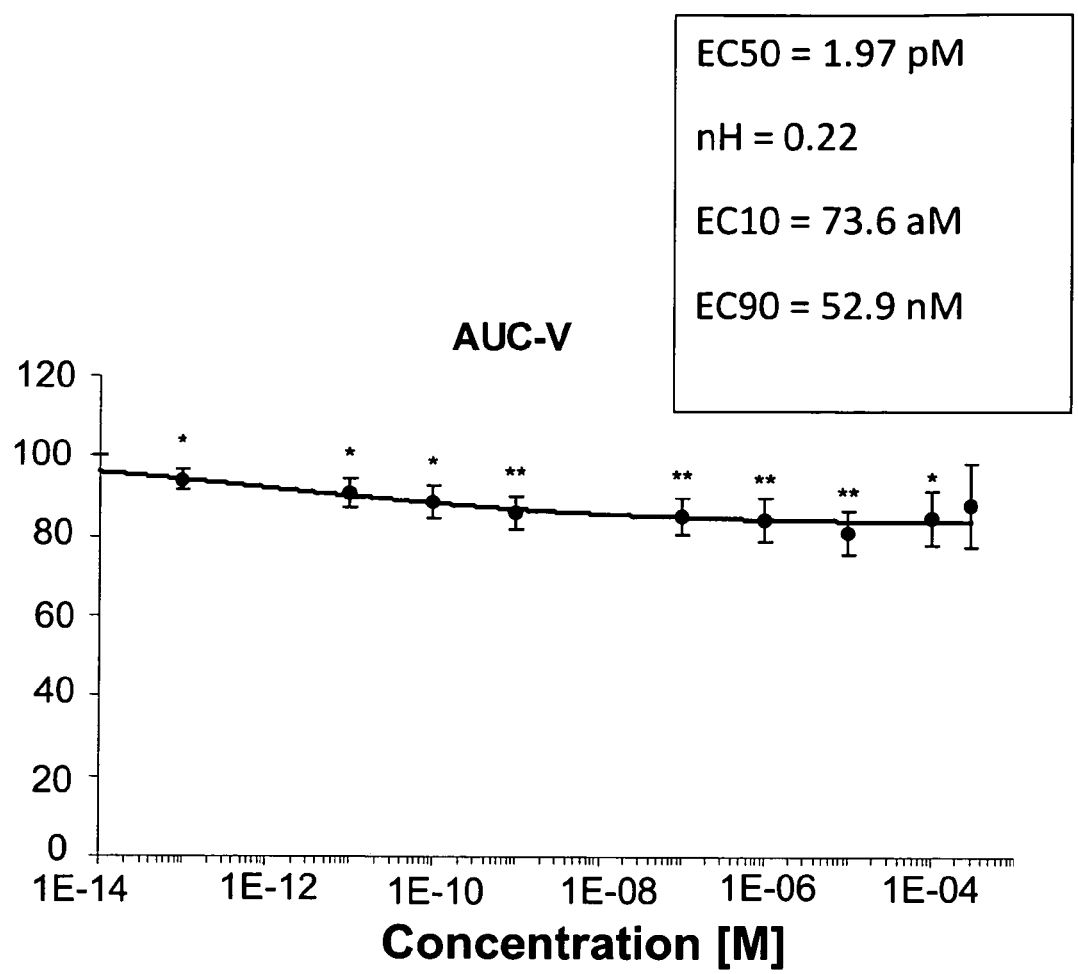
FIG. 6: Acute effects of vicenin 2 (AUC-V) on the cortical network activity in vitro. Plotted are the spike rate changes for treatment of 9 accumulating concentrations in the range of 10 μg/ml to 300 μl/ml (mean±standard error, n=17; Student's paired t-test: * $p \le 0.05$;  $p \le 0.01$; * $p \le 0.001$).

Results:

In general, vicenin 2 has an effect to induce a decrease of the cortical network activity with an $EC_{50}$ at 2 µg/ml and a maximum decrease to 80% of the native activity with no affects on the burst structure, however on the oscillatory behaviour of the network. These results are shown in FIG. 6, which illustrates the concentration depending changes in the activity of the cortical network. It could be seen that vicenin 2 has an influence on the neuroactivity. In a second step this activity was further evaluated by a classification against positive controls.

Classifications

The classification against 105 substances using the electrophysiological multi-channel recording of vicenin 2 and the 105 substances identified several activities for vicenin 2.

Table 1 shows the summaries of the 10 highest-ranking classifications.

TABLE 1

Classification of vicenin 2 (AUC-V) against the NeuroProof database. Shown is a ranking of classification results, which means that x-% of all data records of this substance were classified as the respective substance in the left column; DS corresponds to the relative overall ranking

| | |
|---|---|
| AUC-V, all | 143 |
| reference | # |
| Olanzapine | 17 |
| Eserine | 15 |
| Amisulpride | 15 |
| Enkephalin | 14 |
| Sodium dodecyl sulfate | 12 |
| Atropinemethylbromide | 12 |
| Nicotine | 12 |
| Indatraline | 12 |
| Modafinil | 12 |
| DPDPE | 11 |

For example, it was possible to identify a sedative and anxiolytic activity of vicenin 2 by the classification against Olanzapine and Amisulpride. Olanzapine is a serotonergic agent like 5-$HT_3$ antogonist, 5-$HT_3$ partical agonist and 5-HT4 agonist.

In addition it was also possible to confirm the pain reduction activity of vicenin 2 by classification against enkephalin. Enkephalins are endogenous ligands that bind to the body's opioid receptors leading to antinociceptive activity.

Surprisingly, Vicenin 2 showed also an electrophysiological multi-channel recording comparable with the pattern of the positive control eserine and nicotine. Eserine is a reversible cholinesterase inhibitor and nicotin acts as an acetylcholin agonist.

Results:

The prokinetic effect improves the gastrointestinal mobility by increasing the frequency of contractions in the small intestine, but without changing their rhythm. This leads to a relief from gastrointestinal symptoms, such as abdominal discomfort, bloating, constipation and other symptoms linked to functional dyspepsia or irritable bowel syndrome. Surprisingly, the compound vicenin 2 has prokinetic activity, acting in two different ways. Firstly, as a reversible cholinesterase inhibitor and secondly, as acetylcholine agonist.

Summarizing, the compound vicenin 2 has prokinetic effects by two different mode of actions probably helping when there is an irregular contraction leading to reduced GI mobility and GI symptoms. This effect has previously not been described for any flavonoid glycosides.

Example 3

Vicenin 2 is Effective in Human Individuals

Human study with a standardized *Perilla* leaf extract to investigate the effect of vicenin 2 improvement of intestinal discomfort and bowel function in healthy volunteers with gastrointestinal discomfort Methods and Compound A special *Perilla* leaf extract standardized on vicenin 2 was tested for its effects on improvement of intestinal discomfort and bowel function.

A randomized, placebo-controlled, double blind study was carried out in parallel design. The study population included 50 volunteers, male and female, between 30-70 years, which suffer from gastrointestinal discomfort and have a tendency to constipation. 47 volunteers finished the intervention successfully.

The study consisted of screening, a 2-week run-in phase to measure baseline bowel movements (BM) prior to supplementation phase and a 4-week blinded randomized study product consumption phase.

The outcome was measured with a questionnaire on intestinal symptoms, given in Table 2.

The study preparation was a capsule containing *Perilla frutescens* leaf extract or placebo. The dosage was 2×150 mg per day, corresponding to 24 µg vicenin 2.

TABLE 2

| Questionnaire on intestinal symptoms | |
|---|---|
| Bloating/Distension | 0 = not at all |
| | 1 = very slightly |
| | 2 = slightly |
| | 3 = moderately |
| | 4 = extremely |
| Passage of gas | 0 = not at all |
| | 1 = very slightly |
| | 2 = slightly |
| | 3 = moderately |
| | 4 = extremely |
| Feeling of fullness | 0 = not at all |
| | 1 = very slightly |
| | 2 = slightly |
| | 3 = moderately |
| | 4 = extremely |
| Stomach rumbling | 0 = not at all |
| | 1 = very slightly |
| | 2 = slightly |
| | 3 = moderately |
| | 4 = extremely |
| Abdominal discomfort | 0 = not at all |
| | 1 = very slightly |
| | 2 = slightly |
| | 3 = moderately |
| | 4 = extremely |

Results

*Perilla frutescens* leaf extract at a dosage corresponding to 24 µg vicenin 2 was able to improve the following symptoms of gastrointestinal discomfort: bloating, distension, rumbling, feeling of fullness, abdominal discomfort related to pain and cramps.

Table 3 shows the summary of the results for the study population in comparison to placebo.

V1: Run-in phase
V2: Supplementation phase (week 3+4)

TABLE 3

Results of the volunteer study of vicenin 2 in 47 volunteers.

| | Placebo V1 | Placebo V2 | Perilla V1 | Perilla V2 | Placebo V2-V1 | Perilla V2-V1 |
|---|---|---|---|---|---|---|
| Bloating/Distension | | | | | | |
| Number of values | 23 | 23 | 24 | 24 | 23 | 24 |
| Minimum | 0.1 | 0 | 0 | 0 | −1.86 | −1.93 |
| 25% Percentile | 0.93 | 0.71 | 0.84 | 0.36 | −0.71 | −0.84 |
| Median | 1.50 | 1.00 | 1.47 | 0.93 | −0.14 | −0.36 |
| 75% Percentile | 1.86 | 1.79 | 2.00 | 1.46 | 0.29 | −0.10 |
| Maximum | 3.21 | 3.21 | 3.21 | 3.00 | 0.79 | 0.64 |
| Mean | 1.45 | 1.20 | 1.42 | 0.98 | −0.25 | −0.44 |
| Std. Deviation | 0.74 | 0.77 | 0.81 | 0.78 | 0.71 | 0.56 |
| Std. Error | 0.15 | 0.16 | 0.16 | 0.16 | 0.15 | 0.12 |
| Lower 95% CI of mean | 1.13 | 0.86 | 1.08 | 0.66 | −0.56 | −0.68 |
| Upper 95% CI of mean | 1.77 | 1.53 | 1.76 | 1.31 | 0.06 | −0.20 |
| Passage of gas | | | | | | |
| Number of values | 23 | 23 | 24 | 24 | 23 | 24 |
| Minimum | 0.21 | 0.33 | 0.29 | 0.07 | −1.71 | −1.54 |
| 25% Percentile | 1.07 | 1.00 | 1.09 | 0.88 | −0.57 | −0.93 |
| Median | 1.50 | 1.29 | 1.50 | 1.21 | −0.14 | −0.31 |
| 75% Percentile | 1.86 | 1.64 | 2.14 | 1.84 | 0.43 | 0.07 |
| Maximum | 2.86 | 3.07 | 3.14 | 3.07 | 0.99 | 1.00 |
| Mean | 1.47 | 1.37 | 1.60 | 1.30 | −0.10 | −0.30 |
| Std. Deviation | 0.66 | 0.62 | 0.77 | 0.74 | 0.62 | 0.66 |
| Std. Error | 0.14 | 0.13 | 0.16 | 0.15 | 0.13 | 0.14 |
| Lower 95% CI of mean | 1.18 | 1.10 | 1.27 | 0.98 | −0.37 | −0.58 |
| Upper 95% CI of mean | 1.75 | 1.63 | 1.92 | 1.61 | 0.17 | −0.02 |
| Stomach rumbling | | | | | | |
| Number of values | 23 | 23 | 24 | 24 | 23 | 24 |
| Minimum | 0 | 0.17 | 0 | 0 | −2.07 | −2.5 |
| 25% Percentile | 0.79 | 0.50 | 1.13 | 0.43 | −0.86 | −1.14 |

TABLE 3-continued

Results of the volunteer study of vicenin 2 in 47 volunters.

|  | Placebo V1 | Placebo V2 | Perilla V1 | Perilla V2 | Placebo V2-V1 | Perilla V2-V1 |
|---|---|---|---|---|---|---|
| Median | 1.50 | 0.93 | 1.71 | 0.97 | −0.36 | −0.50 |
| 75% Percentile | 2.14 | 1.93 | 2.31 | 1.63 | 0.29 | 0.12 |
| Maximum | 2.93 | 3.07 | 2.93 | 3.23 | 0.93 | 1.00 |
| Mean | 1.51 | 1.18 | 1.64 | 1.09 | −0.33 | −0.55 |
| Std. Deviation | 0.86 | 0.83 | 0.85 | 0.81 | 0.71 | 0.87 |
| Std. Error | 0.18 | 0.17 | 0.17 | 0.17 | 0.15 | 0.18 |
| Lower 95% CI of mean | 1.14 | 0.82 | 1.28 | 0.74 | −0.64 | −0.92 |
| Upper 95% CI of mean | 1.89 | 1.54 | 2.00 | 1.43 | −0.03 | −0.19 |
| Feeling of fullness | | | | | | |
| Number of values | 23 | 23 | 24 | 24 | 23 | 24 |
| Minimum | 0 | 0.14 | 0 | 0 | −1.71 | −1.86 |
| 25% Percentile | 0.29 | 0.50 | 0.23 | 0.09 | −0.71 | −0.90 |
| Median | 0.93 | 0.64 | 1.11 | 0.54 | −0.07 | −0.36 |
| 75% Percentile | 1.71 | 1.00 | 1.61 | 1.14 | 0.36 | 0.31 |
| Maximum | 2.36 | 2.61 | 2.38 | 1.89 | 0.58 | 0.86 |
| Mean | 1.08 | 0.83 | 1.03 | 0.67 | −0.24 | −0.36 |
| Std. Deviation | 0.80 | 0.62 | 0.77 | 0.63 | 0.64 | 0.72 |
| Std. Error | 0.17 | 0.13 | 0.16 | 0.13 | 0.13 | 0.15 |
| Lower 95% CI of mean | 0.73 | 0.56 | 0.70 | 0.40 | −0.52 | −0.66 |
| Upper 95% CI of mean | 1.42 | 1.10 | 1.35 | 0.93 | 0.03 | −0.05 |
| Abdominal discomfort | | | | | | |
| Number of values | 23 | 23 | 24 | 24 | 23 | 24 |
| Minimum | 0 | 0 | 0 | 0 | −1.36 | −2.43 |
| 25% Percentile | 0.21 | 0.21 | 0.30 | 0.07 | −0.79 | −1.00 |
| Median | 1.43 | 0.79 | 1.22 | 0.33 | 0.00 | −0.36 |
| 75% Percentile | 1.96 | 1.07 | 1.86 | 1.34 | 0.07 | 0.00 |
| Maximum | 2.67 | 3.12 | 2.79 | 2.38 | 0.57 | 0.60 |
| Mean | 1.15 | 0.84 | 1.25 | 0.71 | −0.31 | −0.54 |
| Std. Deviation | 0.93 | 0.81 | 0.86 | 0.74 | 0.55 | 0.75 |
| Std. Error | 0.19 | 0.17 | 0.18 | 0.15 | 0.12 | 0.15 |
| Lower 95% CI of mean | 0.75 | 0.49 | 0.89 | 0.39 | −0.55 | −0.86 |
| Upper 95% CI of mean | 1.55 | 1.19 | 1.61 | 1.02 | −0.07 | −0.23 |
| Summary score GI symptoms question 1-5 | | | | | | |
| Number of values | 23 | 23 | 24 | 24 | 23 | 24 |
| Minimum | 0.29 | 0.21 | 0.21 | 0.1 | −1.67 | −2.25 |
| 25% Percentile | 1.19 | 0.81 | 1.24 | 0.62 | −0.65 | −0.89 |
| Median | 1.53 | 0.97 | 1.63 | 0.96 | −0.30 | −0.45 |
| 75% Percentile | 1.86 | 1.26 | 1.96 | 1.58 | 0.07 | −0.05 |
| Maximum | 2.75 | 2.92 | 2.85 | 2.62 | 0.45 | 0.59 |
| Mean | 1.52 | 1.16 | 1.57 | 1.04 | −0.36 | −0.52 |
| Std. Deviation | 0.64 | 0.62 | 0.64 | 0.62 | 0.54 | 0.65 |
| Std. Error | 0.13 | 0.13 | 0.13 | 0.13 | 0.11 | 0.13 |
| Lower 95% CI of mean | 1.24 | 0.89 | 1.30 | 0.78 | −0.59 | −0.80 |
| Upper 95% CI of mean | 1.79 | 1.43 | 1.84 | 1.31 | −0.12 | −0.25 |

Results

*Perilla frutescens* leaf extract at a dosage corresponding to 24 µg vicenin 2 was able to improve symptoms of gastrointestinal discomfort.

The following symptoms were investigated: bloating, passage of gas, rumbling, feeling of fullness, abdominal discomfort related to pain and cramps.

Volunteers, who took *Perilla* leaf extract, reported a stronger reduction of all five symptoms of gastrointestinal discomfort compared to the placebo group. In particular, ameliorating of bloating, rumbling and abdominal discomfort, like pain and cramps was demonstrated.

Discussion

Consumer research indicates that today one third of consumers who are looking for gut health support do not find an effective product suitable for them. This may be related to the fact that even people with a healthy gut micro flora and no food intolerance suffer from digestive discomfort. Ingredients which work along the brain-gut axes are able to reduce gastrointestinal discomfort, which is triggered by neuronal causes, like e.g. stress.

*Perilla frutescens* leaf extract, corresponding to 24 µg vicenin 2 demonstrated efficacy to reduce bloating, distension, rumbling, feeling of fullness, abdominal discomfort related to pain and cramps.

Summary

Vicenin 2 demonstrated surprisingly antispasmodic and prokinetic efficacy.

The antispasmodic effect was tested within an ex vivo animal study, using isolated rat intestine, example 1. The antispasmodic effect was investigated with respect to the cholinergic system (acetylcholine) and with respect to non-specific contraction mediated by $Ba^{++}$. Vicenin 2 has antispasmodic activity, inhibiting neurotropic and muscolotropic activity.

The neurotropic activity was also confirmed in an in vitro study testing the acute neuroactive effect of vicenin 2 on the neuronal activity of murine frontal cortex networks by means of electrophysiological multi-channel recordings. The electrophysiological multi-channel recording of vicenin 2 showed comparable pattern with the positive control atropinemethylbromide.

In addition, the prokinetic effect based on two different modes of action was found. First, vicenin 2 showed an electrophysiological multi-channel recording comparable with the pattern of the positive control serine for reversible cholinesterase inhibition and secondly, it showed a pattern comparable to nicotine, which acts as an acetylcholin agonist. Both mode of actions increase the activity of the parasympathical system and consequently, lead to higher gastrointestinal activity.

The effect of vicenin 2 was shown in a study of volunteers suffering of gastrointestinal comfort and a tendency to constipation.

The combination of antispasmodic and prokinetic effects lead to beneficial effects supporting gut health.

REFERENCES

1. From the analyst's couch: The IBD market: Nature Reviews Drug Discovery, 5, 99-200, 2006
2. www.theibsnetwork.org
3. Irritable bowel syndrome, Gastroenterology, 60, 1, 2005
4. Irritable bowel syndrome, National Digestive Disease Information Clearinghouse, NIH Publication No. 07-693, 2007
5. The functional gastrointestinal disorder and the Rome III process, D. A. Drossmann, Gastroenterology, 130, 1377-1390, 2006
6. University of Maryland, Medical center, Medical reference for IBS www.umm.edu/altmed/article/irritable-bowel-000098.htm
7. Anti-cancer effects of novel flavonoid vicenin-2 as a single agent and in synergistic combination with docetaxel in prostate cancer. Nagaprashantha L D, et al., Biochem Pharmacol, 7, 2011
8. Vicenin-2, a potential anti-inflammatory constituent of *Urtica circularis*, Marrassini C, et al, J Nat. Prod. 24; 74(6):1503-7, 2011
9. Antinociceptive activity of ethanolic extract and isolated compounds of *Urtica circularis*.
   Gorzalczany S, et al, J. Ethnopharmacol.; 134(3):733-8, 2011
10. Observations concerning the action of 5-hydroxytryptamine on the peristaltic reflex. Bülbring E., et al, Br. J. Pharmacol. 13, 44-57, 1958
11. The effect of intraluminal application of 5-hydroxytryptamine and 5-hydroxytryptophan on peristalsis, the local production of 5-hydroxytryptamine and its release in relation to intraluminal pressure and propulsive activity. Bülbring, E., et al, J. Physiol. (Lond) 140, 381-407, 1958
12. Clinical practice. Irritable bowel syndrome", Mayer E A, N. Engl. J. Med. 358 (16): 1692-9, 2008
13. Flavon C-Glycosides from *Viola yedoensis* Makino, Chen Xie, et al, Chem. Pharm. Bull. 51 (10) 1204-1207, 2003

The invention claimed is:

1. A method for improving condition, the method comprising administering an effective amount of an active ingredient comprising a plant extract enriched for vicenin 2 or an isolated vicenin 2 obtained by isolation or chemical synthesis to a subject in need thereof, wherein said condition is selected from the group consisting of irritable bowel syndrome (IBS), functional dyspepsia (FD), bloating, constipation, diarrhea and visceral hypersensitivity and abdominal pain.

2. The method according to claim 1, wherein the plant extract is in a food product, a dietary supplement or a medicament.

3. The method according to claim 1, wherein a concentration of the active ingredient is from 0.1 µg to 500 µg.

4. The method of claim 1, wherein the administration of the effective amount of the plant extract further provides at least one effect in the subject selected from the group consisting of maintenance of a healthy gut, amelioration of IBS, delaying clinical worsening of functional dyspepsia (FD), ameliorating FD, maintenance of normal digestion, reduction of digestive disorders, balancing of digestive disorders, improvement in gut regularity, healthy gut mobility, healthy bowel movements, healthy stool frequency, healthy stool consistency, healthy stool form, reduction of bloating, reduction of distension, reduction of passage of gas, reduction of stomach rumbling, reduction of a feeling of fullness, improvement in bowel function, amelioration of constipation, amelioration of diarrhea, reduction in visceral hypersensitivity and reduction in abdominal discomfort.

5. The method of claim 4, wherein the abdominal discomfort is selected from the group consisting of pain or cramps.

6. The method of claim 1, wherein a concentration of the active ingredient ranges from 2.5 µg to 50 µg.

7. The method of claim 1, wherein a concentration of the active ingredient ranges from 5 µg to 15 µg.

8. The method of claim 1, wherein a concentration of the active ingredient ranges from 12 µg to 30 µg.

9. The method of claim 1, wherein a concentration of the active ingredient is about 24 µg.

10. The method according to claim 1, wherein the plant extract is obtained from one or more plants selected from the group consisting of *Anethum, Perilla, Camelia, Cayaponia, Cydonia, Colocasia, Desmodium, Hordeurn, Origanum, Ocimum, Jatropha, Parkinsonia, Peperomia, Piheranthos, Centaurea, Indigo, Bomba, Asplenium, Chinotto, Citrus, Viola, Trigonella,* species belonging to Lamiacea, species belonging to Labiatae, Rosemary, Thyme, Basil, Sage, Oregano, *Lavandula, Nipponanthemum, Abrus, Oryza, Seleropyrum, Tulsi, Centaurea, Indigofera, Bombax, Glinus, Rosales, Malpighiales* and combinations thereof.

11. The method according to claim 1, wherein the plant extract is from a preparation selected from the group consisting of a leaf preparation, a fruit preparation, a seed preparation, a stem preparation, a flower preparation, a bud preparation, a root preparation and mixture thereof.

12. The method according to claim 1, wherein the plant extract is selected from the group consisting of a liquid extract and a powder extract.

13. The method according to claim 1, further comprising an agent capable of improving gut health.

14. The method according to claim 13, wherein the agent is selected from the group consisting of a prebiotic agent, fiber, a probiotic agent, a lipid, a physiologically active fatty acid, a sterol, a sterol ester, a bulking agent, a medicament, an antispasmodic agent, an anti-inflammatory agent, a plant phenolic, a phenolic metabolite, an essential oil and a plant preparation.

15. The method according to claim 14, wherein the plant extract is selected from one or more plants selected from the group consisting of *Aloysia triphylia, Hypericum perforatum, serrata, Galanthus nivalis, Salvia officinalis, Panex ginseng, Lippia citriodora, Melissa officinalis, Passiflora incarnate, Passiflora edulis, Bacopa monnieri, Zingiber officinalis, Leucojum aestrum, Concolulus pluricaulis, Centella asiatica, Emblica officinalis, Coptidis Rhizoma, Salvia triloba, Piper nigrum, Trigonella foenum-graecum, Cimicifuga racemosa, Salvia miltiorrhiza, Rhodiola rosea, Habranthus jamesonii, Phycelia herbertiana, Rhodophiala mendocina, Zephyranthes filifolia, Stephania pierrei, Kaempfera parviflora, Stephania venosa, Crocus sativos, Salvia species, Bacopa monnieri, Centella asiatica, Ptychopetalum olacoides,* With-

*ania somnifera, Maytenus ilicifolia, Mentha spicata, Coriandrum sativuni, Urtica Circularis, Lychnophora, Lychnophora trypanocidal, Jodina rhombifolio, Aspalathus linearis, Cyclopia species, Adansonia digitata, Scierocarya birrea, Mangifera indica, Actinidia chinensis, Matricaria recutita, Mentha piperita, Plantago lanceolata, Morinda morindoides, Vitis viniferis, Psidium guajava, Aloysia citriodora, Cordyceps sinensis, Laminaria digitata, Cynara scolymus, Carom carvi, Iberis amara, Angelica archangelica, Silybum marianum, Chelidonium majus, Glycyrrhiza glabra, Vaccinium macrocarpon, Vaccinium myrtillus, Vaccinium corymbosum, Vaccinium ashei, Vaccinium angustifolium, Prunus virginiana, Vaccinium parvifolium, Gaylussacia species, Vaccinium vitis-idaea, Salix* species and combinations thereof.

16. The method according to claim 14, wherein the medicament is selected from the group consisting of a further antispasmodic agent, a tricycle antidepressant, a cholecystokinin-1 antagonist, a serotonergic agent, a benzodiazepine, a benzodiazepine analogue, a neurokinin antagonist, a Guanylate cyclase-C agonist, a C1-C2 channel activator, a Cl secretion blocker, a GLP1 analogue, a κ-opioid agonist, an antacid, a sodium phosphate, a NA reuptake inhibitor, an omeprazol analogue, a glycocorticoid and an antibiotic.

* * * * *

UNITED STATES PATENT AND TRADEMARK OFFICE
CERTIFICATE OF CORRECTION

PATENT NO. : 9,125,926 B2  Page 1 of 1
APPLICATION NO. : 13/997979
DATED : September 8, 2015
INVENTOR(S) : Hajime Fujii et al.

It is certified that error appears in the above-identified patent and that said Letters Patent is hereby corrected as shown below:

Claims
Column 24, line 34, claim 10 insert --Viola, Santalum-- after "Abrus,".
Column 24, line 34, claim 10 "Sel-" should read --Scl- --.
Column 24, line 56, claim 15 "triphylia" should read --triphylla--.
Column 24, line 57, claim 15 insert --Hyperzia-- before "serrata".

Signed and Sealed this
Nineteenth Day of January, 2016

Michelle K. Lee
*Director of the United States Patent and Trademark Office*